(12) United States Patent
Groepl et al.

(10) Patent No.: US 10,211,249 B2
(45) Date of Patent: Feb. 19, 2019

(54) X-RAY DETECTOR HAVING A CAPACITANCE-OPTIMIZED LIGHT-TIGHT PAD STRUCTURE

(71) Applicant: Siemens Healthcare GmbH, Erlangen (DE)

(72) Inventors: Martin Groepl, Sonthofen (DE); Edgar Goederer, Forchheim (DE); Thomas Suttorp, Munich (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/752,932

(22) PCT Filed: Jun. 3, 2016

(86) PCT No.: PCT/EP2016/062650
§ 371 (c)(1),
(2) Date: Feb. 15, 2018

(87) PCT Pub. No.: WO2017/036619
PCT Pub. Date: Mar. 9, 2017

(65) Prior Publication Data
US 2018/0233527 A1 Aug. 16, 2018

(30) Foreign Application Priority Data
Aug. 28, 2015 (DE) .......................... 10 2015 216 527

(51) Int. Cl.
*H01L 27/146* (2006.01)
*H01L 31/08* (2006.01)
(Continued)

(52) U.S. Cl.
CPC .......... *H01L 27/14636* (2013.01); *A61B 6/03* (2013.01); *G01T 1/244* (2013.01);
(Continued)

(58) Field of Classification Search
CPC ..... H01L 27/14636; G01T 1/247; G01T 1/24; G01T 1/242
(Continued)

(56) References Cited

U.S. PATENT DOCUMENTS 6,943,424 B1 * 9/2005 Kim .................. H01L 27/14618
257/433
2004/0195640 A1 10/2004 Nascetti
(Continued)

FOREIGN PATENT DOCUMENTS

| CN | 102544032 A | 7/2012 |
|---|---|---|
| DE | 102012202500 A1 | 8/2013 |
| JP | 2015060909 A | 3/2015 |

OTHER PUBLICATIONS

German Office Action and English translation thereof dated Apr. 1, 2016.
(Continued)

*Primary Examiner* — Kenneth J Malkowski
(74) *Attorney, Agent, or Firm* — Harness, Dickey & Pierce, P.L.C.

(57) ABSTRACT

An x-ray detector includes a substrate including an electrically conductive connection between a read-out contact in the region of the top side of the substrate and an input of a pre-amplifier in an active layer of an integrated circuit. A first electrically conductive connection is provided between the read-out contact and a second electrically conductive connection. A surface of a first light protection is relatively larger than a surface of a light-permeable region of the first light protection. The second electrically conductive connection is provided within a second projection of the surface of the light-permeable region along the surface normal and below the second light protection. A third electrically conductive connection between the second electrically conductive connection and the pre-amplifier is provided below the (Continued)

second light protection. The input of the pre-amplifier is protected against direct incidence of light.

28 Claims, 5 Drawing Sheets

(51) Int. Cl.
    *A61B 6/03*      (2006.01)
    *G01T 1/24*      (2006.01)
    *H01L 23/522*      (2006.01)
    *H01L 23/00*      (2006.01)

(52) U.S. Cl.
    CPC .......... *G01T 1/247* (2013.01); *H01L 23/5225* (2013.01); *H01L 24/16* (2013.01); *H01L 27/14623* (2013.01); *H01L 27/14634* (2013.01); *H01L 27/14659* (2013.01); *H01L 27/14676* (2013.01); *H01L 31/085* (2013.01); *H01L 2224/0557* (2013.01); *H01L 2224/16146* (2013.01)

(58) Field of Classification Search
    USPC ........................................................ 257/292
    See application file for complete search history.

(56) References Cited

U.S. PATENT DOCUMENTS

| | | |
|---|---|---|
| 2008/0230922 A1 | 9/2008 | Mochizuki et al. |
| 2009/0095913 A1 | 4/2009 | Yu |
| 2012/0146016 A1 | 6/2012 | Park et al. |
| 2015/0054110 A1 | 2/2015 | Kashihara |
| 2015/0179691 A1 | 6/2015 | Yanagita |
| 2016/0173803 A1 | 6/2016 | Fukuoka |

OTHER PUBLICATIONS

German Decision to Grant and English translation thereof dated Jul. 12, 2016.
International Search Report PCT/ISA/210 for International Application No. PCT/EP2016/062650 dated Sep. 27, 2016.
Written Opinion of the International Searching Authority PCT/ISA/237 for International Application No. PCT/EP2016/062650 dated Sep. 27, 2016.
German Office Action #102015216527.2 dated Apr. 1, 2016.
Chinese Office Action and English translation dated Nov. 2, 2018.

* cited by examiner

X-RAY DETECTOR HAVING A CAPACITANCE-OPTIMIZED LIGHT-TIGHT PAD STRUCTURE

PRIORITY STATEMENT

This application is the national phase under 35 U.S.C. § 371 of PCT International Application No. PCT/EP2016/062650 which has an International filing date of Jun. 3, 2016, which designated the United States of America and which claims priority to German patent application number DE 102015216527.2 filed Aug. 28, 2015, the entire contents of which are hereby incorporated herein by reference.

FIELD

An embodiment of the invention generally relates to an X-ray detector and a medical apparatus.

BACKGROUND

Appropriate direct-conversion X-ray detectors can be used in the field of X-ray imaging, e.g. computed tomography, angiography or radiography. The X-ray radiation or the photons can be converted into electrical pulses by a suitable sensor. Examples of sensor materials include CdTe, CZT, CdZnTeSe, CdTeSe, CdMnTe, InP, $TlBr_2$, $HgI_2$, GaAs, etc. The electrical pulses are analyzed by evaluation electronics, e.g. an integrated circuit (Application Specific Integrated Circuit: ASIC) in a substrate.

In appropriate X-ray detectors having direct-conversion semiconductor sensors, electron hole pairs are generated by absorption of X-ray quanta in the sensor. The electron hole pairs are separated by an electric field which is applied to the sensor. The charges induce a charge pulse in the electrodes on both sides of the sensor. In the detector elements of the X-ray detector, the charge pulse is carried from a read-out contact to an input of the signal processing chain of the detector element. A first component of this chain is typically a pre-amplifier, e.g. a charge-sensitive pre-amplifier or a transimpedance amplifier. The input capacitance of the pre-amplifier has an influence on its noise characteristic. The input capacitance of the pre-amplifier also has an influence on the design of the pre-amplifier in respect of power consumption and transfer function.

Standard read-out contacts are typically used to connect the sensor to the inputs of the integrated circuit (ASIC) using soldered connections, e.g. solder balls. In this case, for reasons of stability, via connections are often used to connect some or all metal layers below the read-out contact. A via connection is a through-hole. The via connection represents an electrically conductive connection. The via connection can provide an electrically conductive connection between two metal layers or metallization layers. The diameter of the read-out contact is determined by the size of the solder balls to be used as a soldered connection to the sensor. The solder balls are selected to be as large as possible in order to maximize the distance between sensor and top metal layer and therefore to minimize the capacitance between the read-out contact and the integrated circuit.

In order to reduce the capacitance of the via connections below the read-out contact relative to proximate conducting paths in the integrated circuit, a metallization-free zone can be configured around the via connection. Both measures result in a high demand for space for the read-out contact and the structures below it, e.g. via connection and metallization-free zone. In the case of highly integrated pixel electronics with small distances between the individual detector elements, these measures represent a problem. Furthermore, light which has penetrated the sensor can reach into the integrated circuit as a result of the metallization-free zone and influence the analog electronics, e.g. the pre-amplifier. For example, the light can generate charge carriers in the sensitive analog circuits. The response of the sensitive analog amplifier circuits can be changed and degraded thereby.

SUMMARY

The inventors have discovered that a light-tight input into the pre-amplifier is therefore desirable. The inventors have discovered that the light-tight input is important in particular for X-ray detectors in which light, e.g. UV light or visible light, can reach the upper surface of the sensor; and that the requirement for light-tightness makes it difficult to achieve a minimum input capacitance at the same time.

At least one embodiment of the invention specifies an X-ray detector and/or a medical apparatus which allow a light-tight input of the pre-amplifier and a minimum input capacitance of the pre-amplifier.

At least one embodiment of the invention is directed to an X-ray detector and/or a medical apparatus.

At least one embodiment of the invention relates to an X-ray detector comprising a substrate which has an electrically conductive connection between a read-out contact at or in the region of the top side of the substrate and an input of a pre-amplifier in an active layer of an integrated circuit. A first electrically conductive connection is provided between the read-out contact and a second electrically conductive connection. A surface of a first light protection at the top side of the substrate is larger than a surface of a light-permeable region which is in the substrate and laterally delimited by a second light protection, so that the surface of the first light protection covers the surface of the light-permeable region in a first projection along the surface normal. The second electrically conductive connection is provided within a second projection of the surface of the light-permeable region along the surface normal and below the second light protection. A third electrically conductive connection between the second electrically conductive connection and the pre-amplifier is provided below the second light-protection. The input of the pre-amplifier is protected against direct incidence of light.

At least one embodiment further relates to a medical apparatus comprising an X-ray detector according to the invention.

The medical apparatus can be a radiography device, a C-arm angiography system or a computed tomograph. In a preferred embodiment variant, the medical apparatus is a computed tomograph. The advantages of the X-ray detector can be transferred to the medical apparatus. It is advantageously possible to achieve reproducible results or X-ray scans irrespective of a variable incidence of light on the sensor. The X-ray detector can comprise small detector elements and a high spatial resolution can advantageously be achieved.

BRIEF DESCRIPTION OF THE DRAWINGS

Example embodiments of the invention are explained in greater detail below with reference to drawings, in which.

DETAILED DESCRIPTION OF THE EXAMPLE EMBODIMENTS

Figure 1:
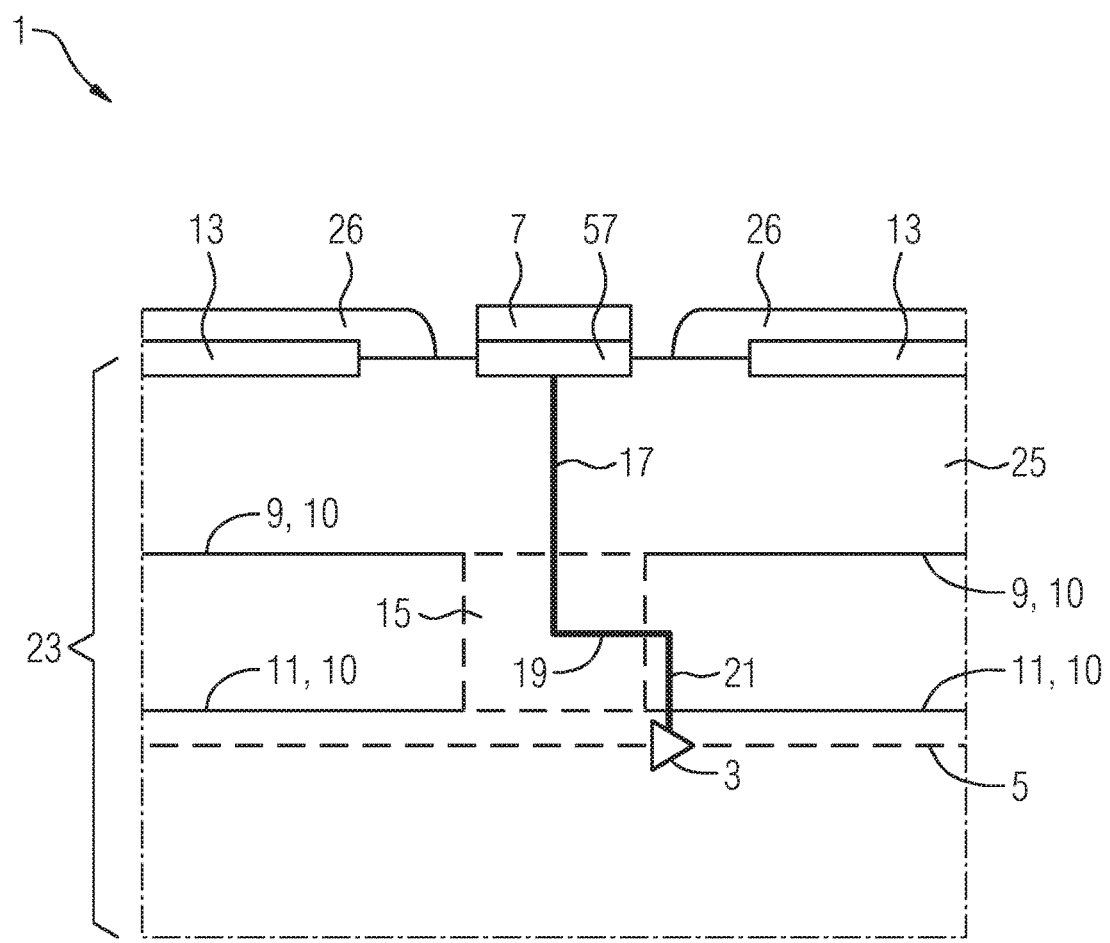
FIG. 1 schematically shows a design of an inventive X-ray detector according to a first embodiment variant.

At least one embodiment of the invention relates to an X-ray detector comprising a substrate which has an electrically conductive connection between a read-out contact at or in the region of the top side of the substrate and an input of a pre-amplifier in an active layer of an integrated circuit. A first electrically conductive connection is provided between the read-out contact and a second electrically conductive connection. A surface of a first light protection at the top side of the substrate is larger than a surface of a light-permeable region which is in the substrate and laterally delimited by a second light protection, so that the surface of the first light protection covers the surface of the light-permeable region in a first projection along the surface normal. The second electrically conductive connection is provided within a second projection of the surface of the light-permeable region along the surface normal and below the second light protection. A third electrically conductive connection between the second electrically conductive connection and the pre-amplifier is provided below the second light-protection. The input of the pre-amplifier is protected against direct incidence of light.

The substrate can comprise the entire volume of an ASIC and the layers built on it, including a first insulation layer, the metal layers and a wafer substrate comprising the active layers. The wafer substrate can be based on silicon, for example. The metal layers can comprise copper or aluminum, for example. The metal layers or metallization layers can be separated from each other by a dielectric such as silicon oxide, for example. The first insulation layer can comprise silicon oxide, for example.

The first light protection can be the read-out contact. The first light protection and the read-out contact can form a unit. In an alternative embodiment variant, the first light protection and the read-out contact do not form a unit, and therefore an electrically conductive connection between the first light protection and the read-out contact can also be provided.

The first light protection can be a different component of the structure to the read-out contact; it can be the soldered connection, for example. The first light protection can comprise a metal. The first light protection can be situated at or in the region of an upper surface of the substrate, the upper surface facing the sensor, e.g. as a unit with the read-out contact. The first light protection can be situated above the read-out contact at the upper surface of the substrate. The first light protection covers the light-permeable region in the first projection, the light-permeable region being laterally delimited by the second light protection.

The opening of the second light protection for delimiting the light-permeable region is smaller than the surface of the first light protection. The surface can represent the surface area.

The first electrically conductive connection can consist of a plurality of parts. The first electrically conductive connection can have an intermediate contact.

The second electrically conductive connection can be connected to the first electrically conductive connection in an electrically conductive manner within the light-permeable region. The second light protection can be a metal layer. The light-permeable region is free of metal layers and ensures a distance between the metal layers and the first electrically conductive connection. The capacitance is advantageously minimized. The coupling of other signals into the input of the pre-amplifier is advantageously reduced or prevented.

The light-permeable region is advantageously situated in that region which is shaded by the first light protection. Below the second light protection, e.g. within the CMOS layers or metal layers, the second electrically conductive connection is connected to the input of the pre-amplifier. The input capacitance of the pre-amplifier is advantageously minimized.

The electrically conductive connection of the read-out contact to the input of the pre-amplifier is referred to as the pad structure, wherein the pad structure includes the read-out contact. The read-out contact can be referred to as a ball pad. An X-ray detector having a capacitance-optimized light-tight pad structure or having a connection of the read-out contact to the input of the pre-amplifier is advantageously achieved.

The pad structure is advantageously impermeable to direct incidence of light. The pad structure is advantageously impermeable to UV light or visible light.

The first electrically conductive connection, the second electrically conductive connection and the third electrically conductive connection can be situated in a shared shade of the first light protection, the second light protection and the third light protection, so that the input of the pre-amplifier is protected against incidence of light in a particularly advantageous manner.

At least one embodiment further relates to a medical apparatus comprising an X-ray detector according to the invention.

The medical apparatus can be a radiography device, a C-arm angiography system or a computed tomograph. In a preferred embodiment variant, the medical apparatus is a computed tomograph. The advantages of the X-ray detector can be transferred to the medical apparatus. It is advantageously possible to achieve reproducible results or X-ray scans irrespective of a variable incidence of light on the sensor. The X-ray detector can comprise small detector elements and a high spatial resolution can advantageously be achieved.

According to an embodiment of the inventive X-ray detector, the read-out contact is the first light protection. The size of the read-out contact can be selected in such a way that it advantageously satisfies the desired size of the solder balls or soldered connections and at the same time advantageously protects the active layers or the input of the pre-amplifier against direct incidence of light.

According to an embodiment of the inventive X-ray detector, the first electrically conductive connection and/or the third electrically conductive connection is a via connection.

The first electrically conductive connection can be formed of multiple parts. The individual parts can have a via connection. The via connections can be embodied as solid or hollow tubular via connections. The via connections can connect a plurality of metal layers in a stacked arrangement. It is advantageously possible to achieve a high degree of stability for the first electrically conductive connection or the second electrically conductive connection.

According to an embodiment of the inventive X-ray detector, the first electrically conductive connection or the third electrically conductive connection is designed at least partly as a multilayer via connection. The multilayer via connections use partial regions of the metal layers, the partial regions being separated horizontally by a distance from the metal layers, e.g. the second light protection. It is advantageously possible to realize connections perpendicular to the metal layers during the deposition of the metal layers. The basal surface of the via connection between the intermediate contact and the second electrically conductive connection can advantageously be smaller than the surface of the intermediate contact.

According to an embodiment of the inventive X-ray detector, a first insulation layer is provided between the top side of the substrate and the second light protection.

A thick first insulation layer can be provided between the top side of the substrate and the second light protection. The insulation layer can be between 10 µm and 200 µm thick, for example. A thick first insulation layer can be provided between the first light protection and the second light protection. The first insulation layer can extend over the entire horizontal width and parallel to the second light protection or the upper surface of the substrate. The first insulation layer can advantageously be deposited in economical or favorable process steps. The first insulation layer can advantageously increase the mechanical stability of the structure. The capacitance of the read-out contact can advantageously be minimized.

According to an embodiment of the inventive X-ray detector, the first electrically conductive connection has an intermediate contact. The second light protection has a plurality of metal layers. The intermediate contact is provided in an upper metal layer.

The intermediate contact can be situated in an upper metal layer. The intermediate contact is preferably situated in the top metal layer, which is closest to the read-out contact and advantageously furthest from the active layers. The intermediate contact is limited to a surface within the metal layer and is surrounded by a gap. The distance between an upper metal layer and the active layers can be small. Size and shape of the intermediate contact can advantageously be selected independently of the read-out contact.

According to an embodiment of the inventive X-ray detector, the intermediate contact has a smaller surface than the read-out contact in a projection along the surface normal.

The surface of the intermediate contact is small and preferably corresponds to a minimum size permitted by the technology. The surface of the intermediate contact is smaller than the read-out contact. The shape of the intermediate contact can be round or angular. In a preferred embodiment variant, the read-out contact is less than 50 percent of the surface of the read-out contact. The size of the intermediate contact can advantageously be selected to be smaller than the size of the read-out contact. The distance between an upper metal layer and the active layers can be small. The capacitance, in particular the parasitic capacitance, can advantageously be reduced as a result of the small surface of the intermediate contact in comparison with the read-out contact. As a result of the small size of the intermediate contact, more space per detector element is advantageously available for circuits. If it is prohibited to position circuits below a contact, e.g. the intermediate contact, the smaller size of the intermediate contact is particularly advantageous because the prohibited region is reduced in size. The size of the intermediate contact can advantageously be selected to be considerably smaller than the size of the read-out contact or the size of the solder ball or the soldered connection. The size of the intermediate contact can be in the range of 10 µm to 50 µm, for example.

According to an embodiment of the inventive X-ray detector, the first electrically conductive connection advantageously connects the read-out contact to the second electrically conductive connection in an electrically conductive manner.

According to an embodiment of the inventive X-ray detector, the first electrically conductive connection includes a via connection between the read-out contact and the intermediate contact, the intermediate contact, and a multilayer via connection between the intermediate contact and the second electrically conductive connection. In other words, a via connection between the read-out contact and the intermediate contact, the intermediate contact itself, and a multilayer via connection between the intermediate contact and the second electrically conductive connection can together form the first electrically conductive connection or parts thereof.

The first electrically conductive connection can comprise the intermediate contact. The read-out contact and the intermediate contact can be connected by way of a via connection. This via connection can be part of the first electrically conductive connection. The intermediate contact can further be connected by way of a multilayer via connection to the second electrically conductive connection, the second electrically conductive connection being situated in a lower metal layer. The multilayer via connection can have a round or angular basal surface. In a preferred embodiment variant, the basal surface can be a polygon, e.g. an octagon. The basal surface can advantageously be selected to be smaller than the surface of the intermediate contact, such that adequate mechanical stability is nonetheless ensured.

According to an embodiment of the inventive X-ray detector, an active layer of the integrated circuit is protected against direct incidence of light from the top side by the first light protection, the second light protection or a third light protection.

The generation of charge carriers in the sensitive analog circuits or in the vicinity of the active layers is advantageously reduced or prevented. The response of the sensitive analog amplifier circuits can advantageously be stabilized thereby.

The third light protection can provide a feedthrough of the third electrically conductive connection. The third light protection delimits the light-permeable region above the active layer, so that the active layer is advantageously protected against incidence of light.

According to an embodiment of the inventive X-ray detector, the second light protection or the third light protection is a metal layer. A metal layer can advantageously be used as a light protection by suitable positioning and distance from the active layer. Advantageously, no additional process steps are required during the manufacture.

According to an embodiment of the inventive X-ray detector, the third light protection has a gap. The gap can advantageously minimize the input capacitance of the preamplifier. The gap in this case lies within a shaded region, e.g. in a projection of the surface of the read-out contact or of the intermediate contact along the surface normal. The surface of the gap can be smaller than the surface of the read-out contact or of the intermediate contact, so that the active layers are advantageously protected against incidence of light.

According to an embodiment of the inventive X-ray detector, the third light protection is a metal layer below the second light protection. This metal layer can be embodied such that the light-permeable region is delimited towards the active layer. Incidence of light into the active layer is advantageously prevented. This metal layer is impermeable to light.

According to an embodiment of the inventive X-ray detector, the second electrically conductive connection is designed as a metal layer. The second electrically conductive connection can advantageously be manufactured within a process step for manufacturing a metal layer. The second electrically conductive connection is separated and distanced from other regions of the metal layer by way of insulating material.

According to an embodiment of the inventive X-ray detector, a fourth light protection is provided at the top side of the substrate. The fourth light protection can be an outer wiring layer. The fourth light protection can be metallic and advantageously impermeable to light. The fourth light protection can advantageously protect against incidence of light. Non-perpendicular incidence of light on the upper surface can advantageously be prevented from reaching into the light-permeable region. The parasitic capacitance of the fourth light protection is advantageously reduced by the first insulation layer.

According to an embodiment of the inventive X-ray detector, a second insulation layer is provided at the top side of the substrate and outside the surface of the read-out contact, and the fourth light protection is covered at least partly by the second insulation layer. The fourth light protection is advantageously protected against influences from outside the substrate. The second insulation layer and the fourth light protection advantageously contribute to the mechanical stability.

According to an embodiment of the inventive X-ray detector, the first light protection, the first insulation layer, the second light protection and the pre-amplifier are sequentially disposed in a stacked arrangement. The top side of the substrate faces towards the sensor, and therefore the first light protection is situated at the top. The pre-amplifier is situated at the bottom relative to the first light protection, or below the first light protection, and therefore in the opposite direction relative to the sensor. The individual components of the stacked arrangement can have different horizontal and vertical extents. The first light protection and the second light protection are so arranged relative to the light-permeable region and the input of the pre-amplifier that the input of the pre-amplifier is protected against direct incidence of light.

According to an embodiment of the inventive X-ray detector, an upper metal layer, a middle metal layer and a lower metal layer are disposed in a stacked arrangement between the first insulation layer and the active layers.

The upper metal layer is situated at a shorter distance from the top side of the substrate or from the sensor than the middle metal layer or the lower metal layer. The upper metal layer, the middle metal layer and the lower metal layer are impermeable to light. The first electrically conductive connection, the second electrically conductive connection and the third electrically conductive connection can advantageously be manufactured at least partly during the manufacturing steps for manufacturing the metal layers.

According to an embodiment of the inventive medical apparatus, the medical apparatus is a computed tomograph. The response of the sensitive analog amplifier circuits can advantageously be stabilized for all projections or scans. The reconstructed layer images with three-dimensional or four-dimensional representation can advantageously be provided in an image quality which is independent of the incidence of light.

FIG. 1 shows an example embodiment of an inventive X-ray detector 1 according to a first embodiment variant. The substrate 23 includes the entire volume of an ASIC and the layers built on it, including a first insulation layer 25, the metal layers 10 and a wafer substrate comprising the active layer 5. The wafer substrate is based on silicon, for example. The metal layers 10 comprise copper or aluminum, for example. The metal layers 10 or metallization layers are separated from each other by a dielectric such as silicon oxide, for example.

The first insulation layer 25 can comprise silicon oxide, for example. The first light protection 7 is situated above the read-out contact 57. The read-out contact 57 is at the upper surface of the substrate 23. The first light protection 7 and the read-out contact 57 can form a unit.

The first light protection 7 is connected by way of the read-out contact 57, a first electrically conductive connection 17, a second electrically conductive connection 19 and a third electrically conductive connection 21 to the pre-amplifier 3 in an electrically conductive manner. The first light protection 7 includes a metal. The pre-amplifier 3 is situated in the active layer 5.

The X-ray detector 1 further includes the second light protection 9, which laterally delimits the light-permeable region 15. The first electrically conductive connection 17 is situated at least partly within the first insulation layer 25 and the light-permeable region 15. The second electrically conductive connection 19 is situated at least partly in the light-permeable region 15 and in a region below the second light protection 9. The region below the second light protection is the region within a projection of the second light protection 9 along the surface normal.

The third electrically conductive connection 21 connects the second electrically conductive connection 19 to the pre-amplifier 3 in an electrically conductive manner. The third electrically conductive connection is situated below the second light protection 9.

Between the second light protection 9,10 and the active layer 5 is situated the third light protection 10,11. This has a feedthrough for the third electrically conductive connection 21. A fourth light protection 13 is situated at the upper surface of the substrate 23. A second insulation layer 26 is situated over the fourth light protection 13 at the upper surface of the substrate 23 and on the upper surface of the substrate 23, wherein a gap is left for the first light protection 7.

Figure 2:
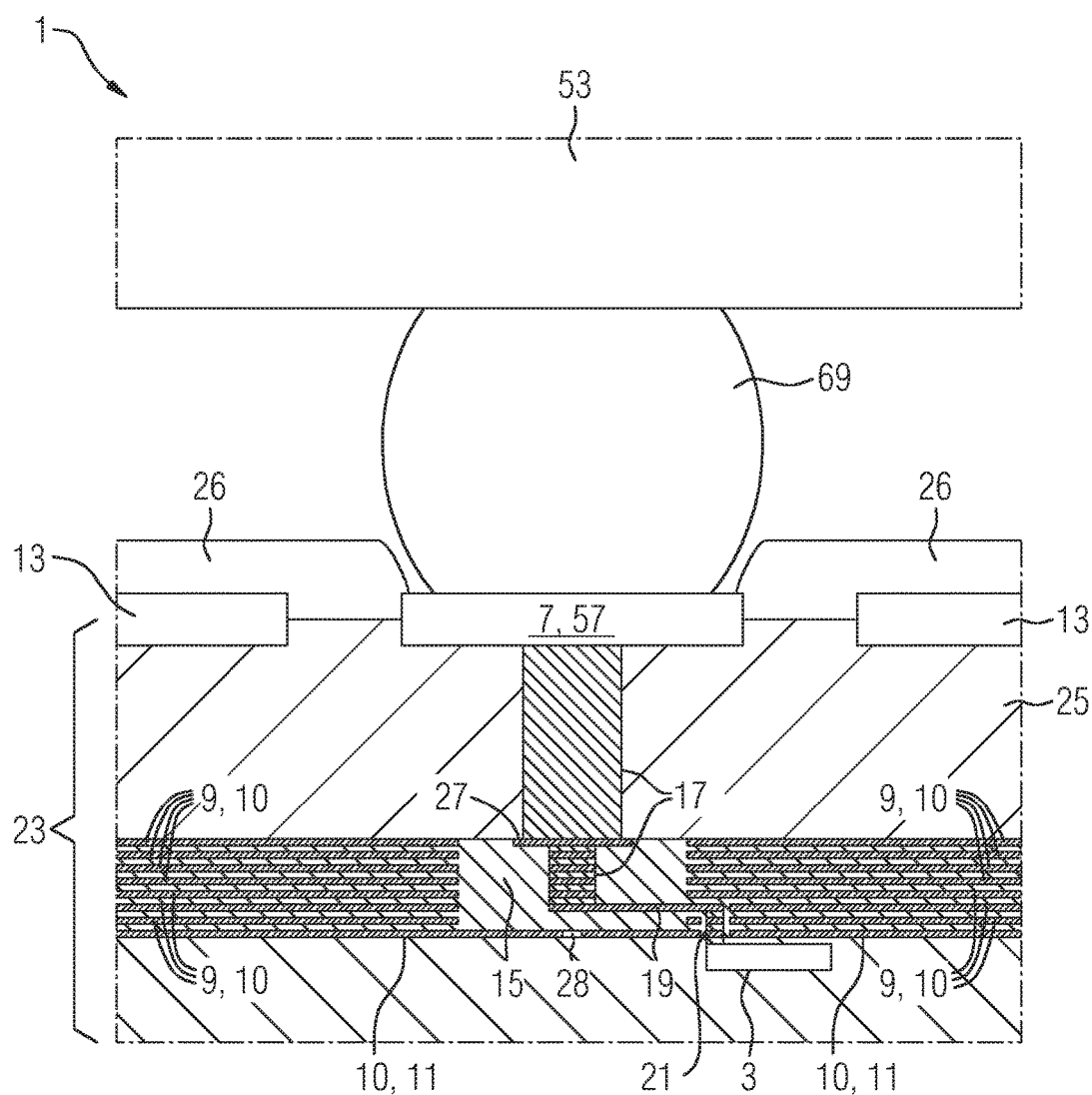
FIG. 2 schematically shows a design of an inventive X-ray detector according to a second embodiment variant.

FIG. 2 shows an example embodiment of an inventive X-ray detector 1 according to a second embodiment variant. The X-ray detector 1 has a sensor 53 comprising CdTe, CZT, CdZnTeSe, CdTeSe, CdMnTe, InP, TlBr$_2$, HgI$_2$ or GaAs, for example, and a substrate 23 comprising an active layer 5. The sensor 53 is connected to the read-out contact 7, 57 in an electrically conductive manner via a soldered connection 69, e.g. a solder ball or a pillar-shaped connection containing copper (copper pillar, not shown). The read-out contact 57 forms a unit with the first light protection 7. The read-out contact 7, 57 therefore jointly forms the first light protection 7.

The fourth light protection 13 is situated at the upper surface of the substrate 23. The second insulation layer 26 covers the fourth light protection 13 and at least partly the upper surface of the substrate 23. The fourth light protection 13 is an outer wiring layer. Below the read-out contact 7, 57, the fourth light protection 13 and the second insulation layer 26 is situated the first insulation layer 25.

The first insulation layer is delimited downwards by the second light protection 25 and the light-permeable region 15. The second light protection 9,10 includes a plurality of layers. The top layer of the second light protection 9,10 is part of the top metal layer 10.

The intermediate contact 27 is likewise part of the top metal layer 10. The surface of the intermediate contact 27 is smaller than the surface of the read-out contact 7, 57. The read-out contact 7, 57 is connected to the intermediate contact 27 in an electrically conductive manner by way of a via connection which is part of the first electrically conductive connection 17.

The light-permeable region 15 is delimited laterally by the multiple layers of the second light protection 9, 10. Within the light-permeable region 15, the intermediate contact is connected to the second electrically conductive connection 19 in an electrically conductive manner by way of a multilayer via connection which is part of the first electrically conductive connection 17. The second electrically conductive connection 19 connects the first electrically conductive connection 17 to the third electrically conductive connection 21, which is situated below the second light protection 9,10. The input of the pre-amplifier 3 is situated below the third light protection 10,11.

The third light protection 10,11 is situated below the multiple layers of the second light protection 9,10. The third electrically conductive connection 21 connects the second electrically conductive connection 19 to the input of the pre-amplifier 3 in the active layer 5. The third light protection, which includes a gap 28, is formed below the intermediate contact 27 and below the multilayer via connection that is part of the first electrically conductive connection 17.

Figure 3:
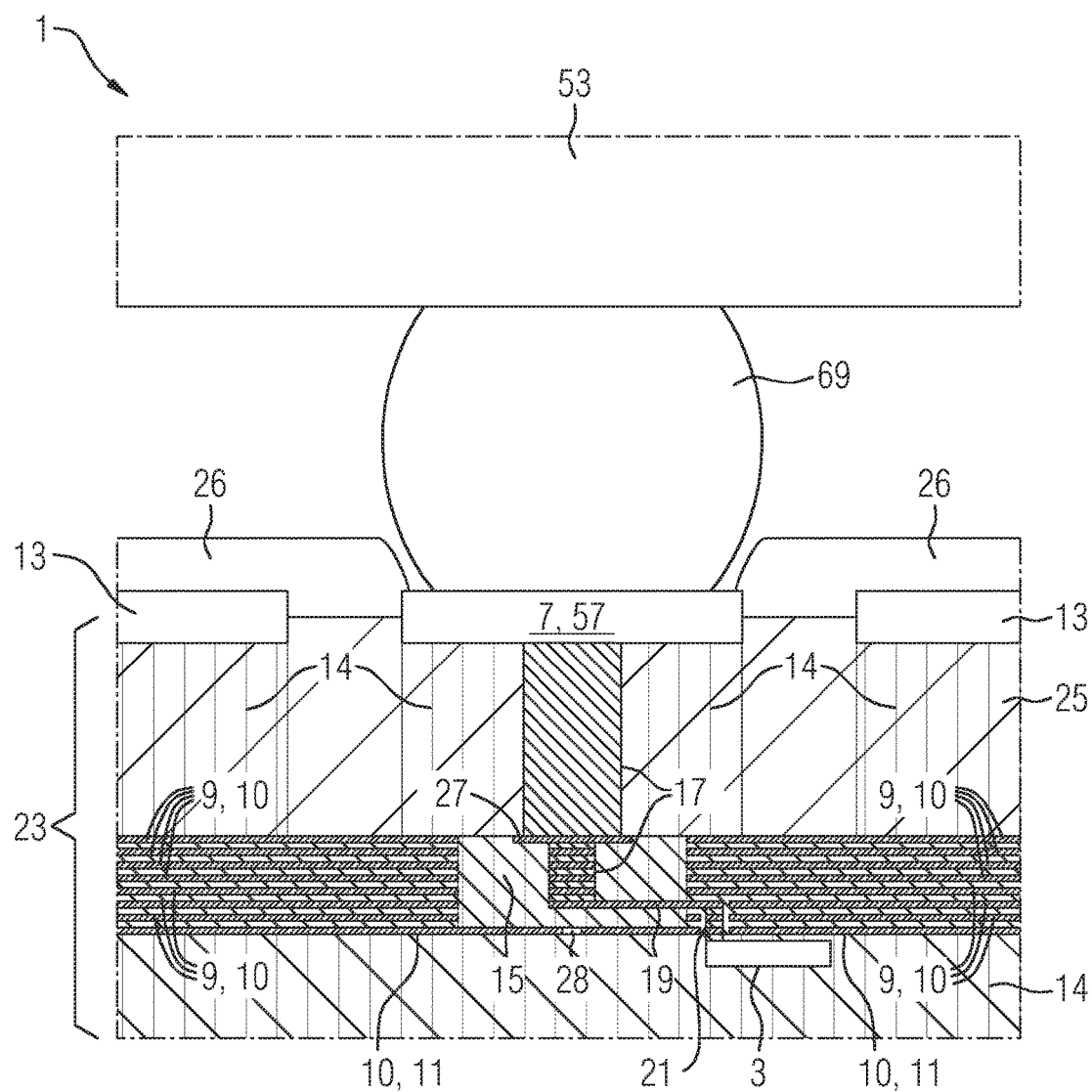
FIG. 3 schematically shows a design of an inventive X-ray detector according to a third embodiment variant.

FIG. 3 shows an example embodiment of an inventive X-ray detector according to a third embodiment variant. In a projection along the surface normal, the first light protection 7 as a unit with the read-out contact 57, the second light protection 9,10, the third light protection 10,11 and the fourth light protection 13 throw shadows 14 so that complete shading of the active layers 5 is achieved.

Figure 4:
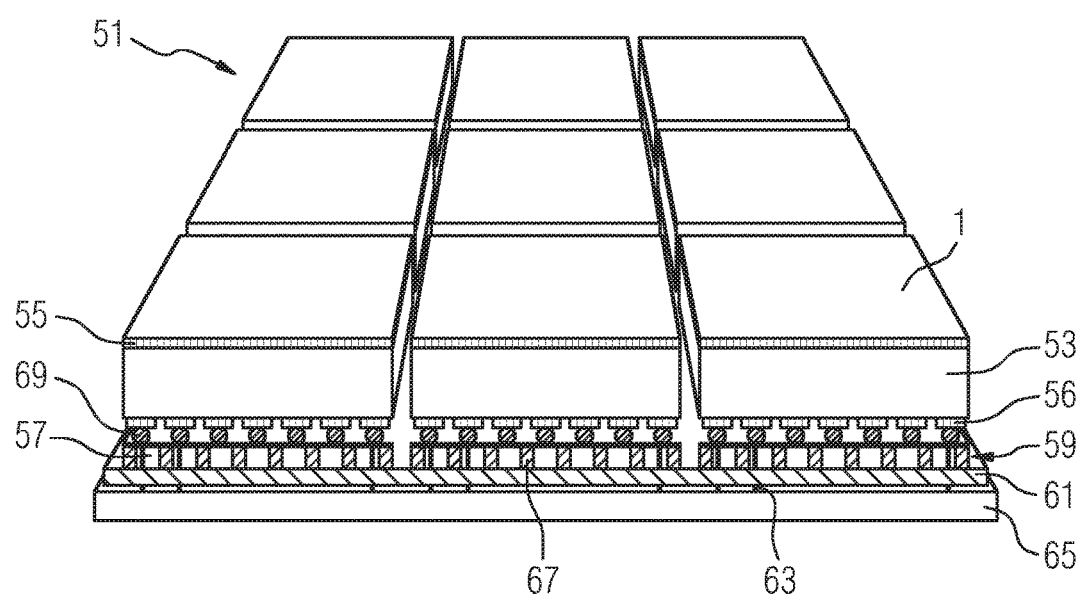
FIG. 4 schematically shows a detector module with an arrangement of inventive X-ray detectors.

FIG. 4 shows an example embodiment of a detector module 51 with an arrangement of inventive X-ray detectors 1. In a preferred embodiment variant, the X-ray detector 1 has a two-dimensional matrix or arrangement of a plurality of pixels or subpixels. The number of subpixels can be in the range of 100 to multiple thousands, for example. The X-ray detector 1 has a sensor 53.

The sensor 53 can be designed as an extended direct converter comprising as converter material, for example, CdTe, CZT, CdZnTeSe, CdTeSe, CdMnTe, InP, TlBr2, HgI2, GaAs, etc. The top side of the sensor 53 has a top electrode 55. The underside of the sensor 53 has a two-dimensional arrangement of contacts 56.

The contacts 56 are connected via soldered connections 69 to the read-out contacts 57 and the pixel electronics 67 in the substrate 59. The soldered connections 69 can be designed as solder balls (bump bonds) or solder material in connection with copper pillars. The number of contacts 56, the number of soldered connections 69, the number of read-out contacts 57 and the number of pixel electronics 67 in the substrate 59 are identical. The electrical field between the top electrode 55 and a contact 56 defines a sensitive detection volume.

The unit comprising a detection volume, a contact 56, a soldered connection 69, a read-out contact 57 and a pixel electronic 67 connected to the read-out contact 57 forms a pixel or subpixel. The underside of the substrate 59 is connected to a support plate 61. The substrate 59 is connected via TSV connections 63 through the support plate 61 to peripheral electronics 65. The substrate 59 has an electrically conductive connection between a read-out contact 57 at the top side of the substrate 23 and an input of a pre-amplifier 3 in an active layer 5 of an integrated circuit having the inventive capacitance-optimized light-tight pad structure.

Figure 5:
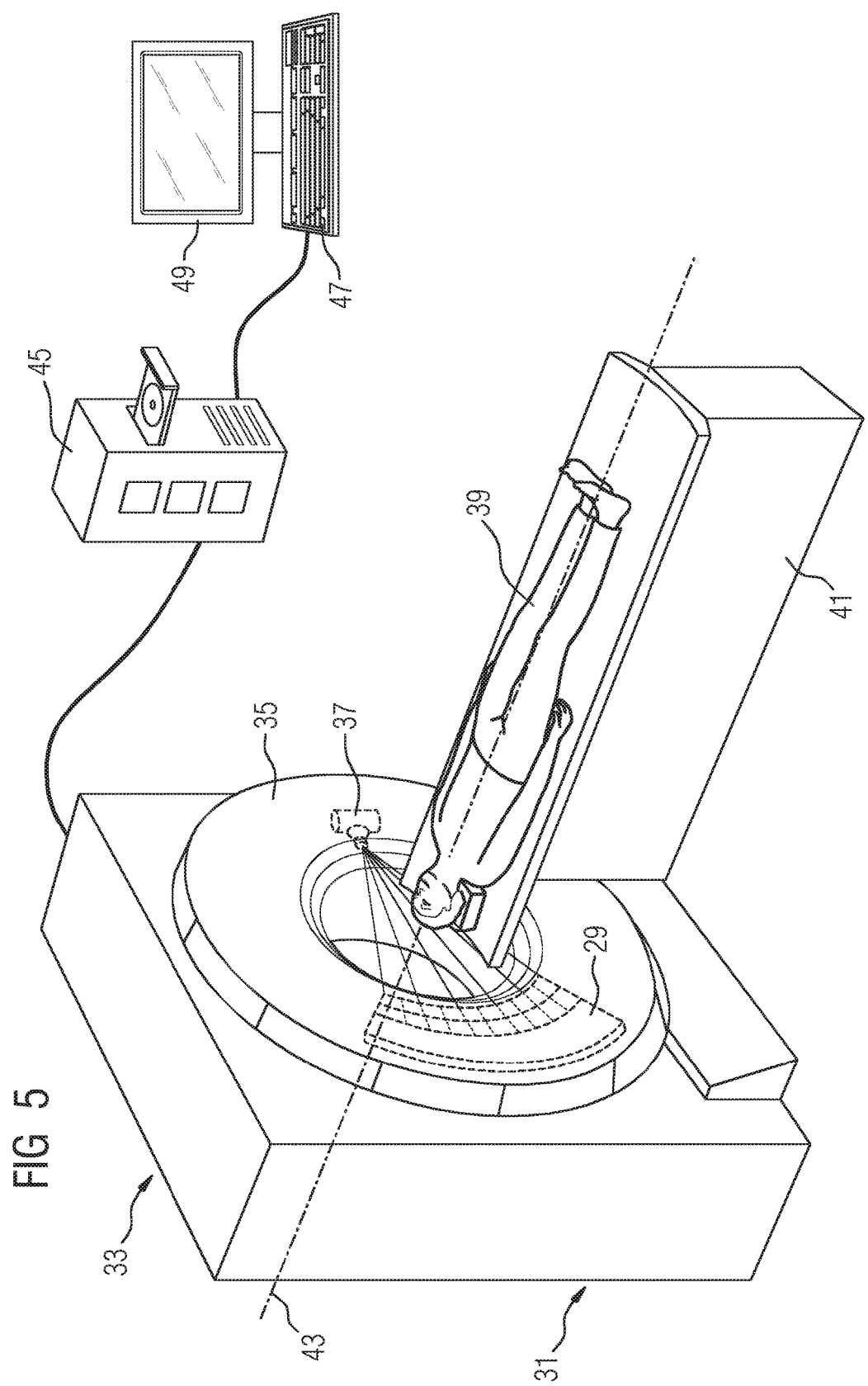
FIG. 5 schematically shows an illustration of an inventive computed tomograph.

FIG. 5 shows an example embodiment of an inventive computed tomograph 31 having an inventive detector device 29. The detector device 29 includes the inventive X-ray detector 1. The detector device 29 can have a plurality of detector modules 51 which have at least one X-ray detector 1. The detector modules 51 preferably have a plurality of X-ray detectors 1 in a two-dimensional matrix or arrangement. The computed tomograph 31 includes a gantry 33 with a rotor 35. The rotor 35 includes an X-ray source 37 and the inventive detector device 29. The patient 39 is supported on the patient couch 41 and can be moved through the gantry 33 along the axis of rotation z 43. A computing unit 45 is used for the purpose of controlling and calculating the sectional images. An input device 47 and an output device 49 are connected to the computing unit 45.

Although the invention is illustrated in detail here with reference to the preferred example embodiment, the invention is not restricted by the examples disclosed and other variations can be derived therefrom by a person skilled in the art without thereby departing from the scope of the invention.

The invention claimed is:
1. An X-ray detector, comprising:
a substrate, including an electrically conductive connection between a read-out contact, and including an electrically conductive connection to a sensor via a soldered connection, in a region of a top side of the substrate and an input of a pre-amplifier in an active layer of an integrated circuit,
a first electrically conductive connection being provided between the read-out contact and a second electrically conductive connection, wherein a surface of a first light protection at the top side of the substrate is relatively larger than a surface of a light-permeable region in the substrate and laterally delimited by a second light protection such that the surface of the first light protection covers the surface of the light-permeable region in a first projection along the surface normal and the light-permeable region is situated in a region shaded by the first protection, the first light protection being situated above the read-out contact at an upper surface of the substrate or the first light protection forming a unit with the read-out contact,
the second electrically conductive connection being provided within a second projection of the surface of the light-permeable region along a surface normal and below the second light protection,
a third electrically conductive connection, between the second electrically conductive connection and the pre-amplifier, being provided below the second light protection, and
the first electrically conductive connection and the third electrically conductive connection are via connections,
such that the input of the pre-amplifier is protected against direct incidence of light.

2. The X-ray detector of claim 1, wherein the read-out contact is the first light protection.

3. The X-ray detector of claim 1, wherein the first electrically conductive connection or the third electrically conductive connection that is a via connection is designed at least partly as a multilayer via connection.

4. The X-ray detector of claim 1, wherein a first insulation layer is provided between the top side of the substrate and the second light protection.

5. The X-ray detector of claim 1, wherein the first electrically conductive connection includes an intermediate contact, the second light protection includes a plurality of metal layers, and the intermediate contact is provided in an upper metal layer.

6. The X-ray detector of claim 5, wherein the intermediate contact includes a relatively smaller surface than the read-out contact in a projection along the surface normal.

7. The X-ray detector of claim 1, wherein the first electrically conductive connection connects the read-out contact to the second electrically conductive connection in an electrically conductive manner.

8. The X-ray detector of claim 5, wherein the first electrically conductive connection includes a via connection between the read-out contact and the intermediate contact, the intermediate contact, and a multilayer via connection between the intermediate contact and the second electrically conductive connection.

9. The X-ray detector of claim 1, wherein an active layer of the integrated circuit is protected against direct incidence of light from the top side by the first light protection, the second light protection or a third light protection.

10. The X-ray detector of claim 9, wherein the second light protection or the third light protection is a metal layer.

11. The X-ray detector of claim 9, wherein the third light protection includes a gap.

12. The X-ray detector of claim 9, wherein the third light protection is a metal layer below the second light protection.

13. The X-ray detector of claim 1, wherein the second electrically conductive connection is designed as a metal layer.

14. The X-ray detector of claim 4, wherein a fourth light protection is provided at the top side of the substrate.

15. The X-ray detector of claim 14, wherein a second insulation layer is provided at the top side of the substrate and outside the surface of the read-out contact, and wherein the fourth light protection is covered at least partly by the second insulation layer.

16. The X-ray detector of claim 4, wherein the first light protection, the first insulation layer, the second light protection, and an active layer including the pre-amplifier are sequentially disposed in a stacked arrangement.

17. The X-ray detector of claim 16, wherein an upper metal layer, a middle metal layer and a lower metal layer are disposed in a stacked arrangement between the first insulation layer and the active layer.

18. A medical apparatus comprising
the X-ray detector of claim 1.

19. The medical apparatus of claim 18, wherein the medical apparatus is a computed tomograph.

20. The X-ray detector of claim 2, wherein the first electrically conductive connection or the third electrically conductive connection that is a via connection is designed at least partly as a multilayer via connection.

21. The X-ray detector of claim 2, wherein a first insulation layer is provided between the top side of the substrate and the second light protection.

22. The X-ray detector of claim 2, wherein the first electrically conductive connection includes an intermediate contact, the second light protection includes a plurality of metal layers, and the intermediate contact is provided in an upper metal layer.

23. The X-ray detector of claim 22, wherein the intermediate contact includes a relatively smaller surface than the read-out contact in a projection along the surface normal.

24. The X-ray detector of claim 1, wherein a fourth light protection is provided at the top side of the substrate.

25. A medical apparatus comprising
the X-ray detector of claim 2.

26. A medical apparatus comprising
the X-ray detector of claim 4.

27. The medical apparatus of claim 25, wherein the medical apparatus is a computed tomograph.

28. The medical apparatus of claim 26, wherein the medical apparatus is a computed tomograph.

* * * * *